(12) United States Patent
Stengele et al.

(10) Patent No.: US 7,687,618 B2
(45) Date of Patent: Mar. 30, 2010

(54) METHOD OF MANUFACTURING LABELLED OLIGONUCLEOTIDE CONJUGATES

(75) Inventors: Klaus Peter Stengele, Pleiskirchen (DE); Evgueni Kvassiouk, Waldkraiburg (DE)

(73) Assignee: NIMBLEGEN SYSTEMS GmbH, Pleiskirchen (DE)

( * ) Notice: Subject to any disclaimer, the term of this patent is extended or adjusted under 35 U.S.C. 154(b) by 1133 days.

(21) Appl. No.: 10/531,292

(22) PCT Filed: Oct. 14, 2003

(86) PCT No.: PCT/EP03/11354

§ 371 (c)(1), (2), (4) Date: Nov. 21, 2005

(87) PCT Pub. No.: WO2004/035600

PCT Pub. Date: Apr. 29, 2004

(65) Prior Publication Data

US 2006/0122382 A1    Jun. 8, 2006

(30) Foreign Application Priority Data

Oct. 14, 2002    (DE) .............................. 102 47 790

(51) Int. Cl.
*C07H 21/00* (2006.01)
*C12Q 1/68* (2006.01)
*C07H 21/02* (2006.01)
*C07H 19/04* (2006.01)

(52) U.S. Cl. .................... 536/25.3; 536/23.1; 536/26.6; 435/6

(58) Field of Classification Search ............... 536/23.1, 536/25.3, 26.6; 435/6
See application file for complete search history.

(56) References Cited

U.S. PATENT DOCUMENTS

| 5,703,218 A | 12/1997 | Horn et al. |
| 5,840,879 A | 11/1998 | Wang |
| 7,183,405 B2 * | 2/2007 | Chiarello et al. ........... 536/25.3 |

FOREIGN PATENT DOCUMENTS

| DE | 69319336 | 6/1998 |
| DE | 3824110 | 7/1998 |
| DE | 69411891 | 7/1998 |
| DE | 19915867 | 4/1999 |
| DE | 19938092 | 8/1999 |

OTHER PUBLICATIONS

Habus I. et al.: "Syntheis of Di-, Tri-, and Tetrameric Building Blocks With Novel Carbamate Internucleoside Linkages and Their Incorporation Into Oligonucleotides" Bio-Organic & Medicinal Chemistry Letters, vol. 4, No. 8, 1994, pp. 1065-1070.

* cited by examiner

*Primary Examiner*—Jezia Riley
(74) *Attorney, Agent, or Firm*—Millen, White, Zelano & Branigan, P.C.

(57) ABSTRACT

The present invention relates to a method for the manufacture of labeled oligonucleotide conjugates comprising the reaction of (a) an oligonucleotide having a labile protecting group bound to a terminal hydroxy group, and (b) a labeling compound, wherein said labile protecting group is partially or completely substituted by said labeling compound in a nucleophilic substitution reaction.

Figure 1:
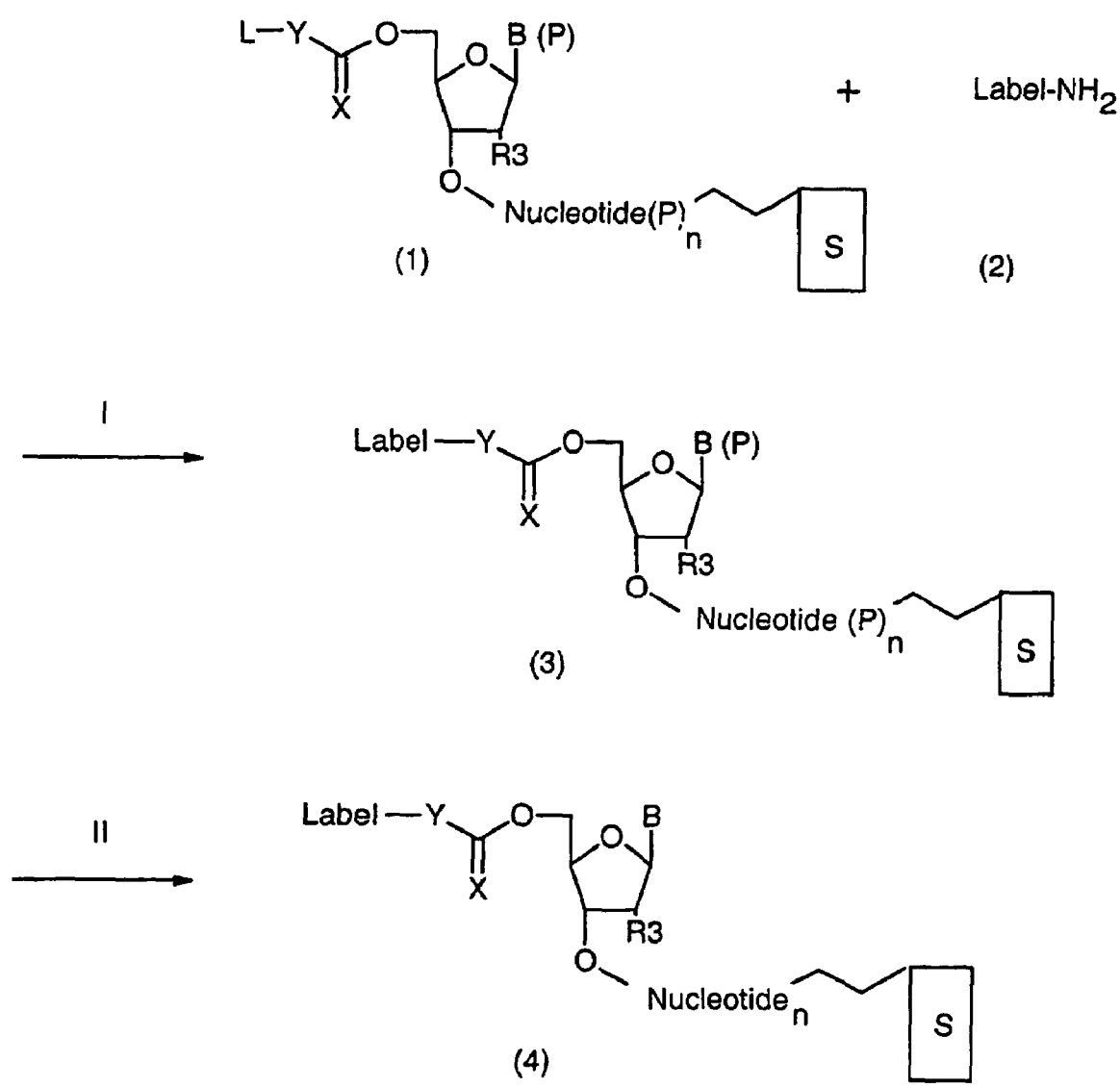

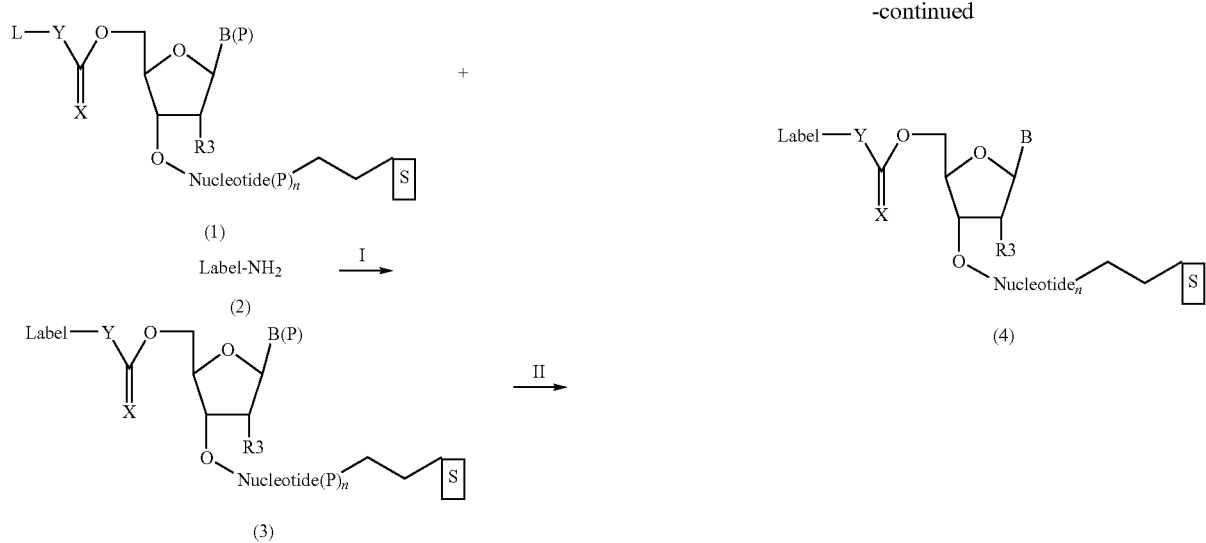
9 Claims, 1 Drawing Sheet

METHOD OF MANUFACTURING LABELLED OLIGONUCLEOTIDE CONJUGATES

The present invention relates to a method for the manufacture of labeled oligonucleotide conjugates comprising the reaction of (a) an oligonucleotide on a solid support having a labile orthogonal protecting group bound to a terminal hydroxy group, and (b) a labeling compound, wherein said labile protecting group is partially or completely substituted by said labeling compound in a nucleophilic substitution reaction.

Synthetic oligonucleotides have been used in all fields of genetic engineering such as in gene transfection or gene analysis. Polynucleotides are prepared by chain extension of a starter compound by sequentially reacting a number of single nucleoside building blocks. For synthesis, the hydroxy groups, that are to be reacted with each other, are derivatized in such a manner that a phosphoric diester group or phosphoric triester group or H phosphonate group is formed between individual nucleoside building blocks during the reaction. Other functional groups of the starter compound and the building blocks that might interfere with the reaction are masked by protecting groups that are typically used for this purpose.

For example, DE 199 15 867 A1 and DE 199 38 092 A1 describe photolabile protecting groups for hydroxy groups that may be introduced into a nucleoside or a nucleotide in high yields and release the protected hydroxy group once electromagnetic radiation in the UV/VIA range is supplied.

Today, oligonucleotides and polynucleotides are commonly prepared with improved efficiency via solid-phase synthetic methods. The starter compounds are bound directly to functionalized solid surfaces of polymer particles or glass, metal or plastic surfaces or via linkers and reacted with the reagents required for polynucleotide chain extension. Excess reagents as well as soluble reaction by-products and solvents can easily be removed from the solid-phase bonded polynucleotide compounds.

Oligonucleotides prepared in this way are often further functionalized (e.g. provided with a haptene) by means of downstream reaction steps after the actual synthesis in order to enable their intended use in biological or biochemical reactions. The term "haptene" refers to a molecular moiety that modifies the physical, chemical and biological properties of the oligonucleotide.

Haptenes are predominantly used for characterizing and identifying the oligonucleotide in a biological assay, for example, by direct optical detection methods or mass spectrometry, or by indirect detection, e.g secondary detection via antibodies. However, it is also common practice to functionalize the oligonucleotide by means of linkers, adaptors, spacers and the like, so that, for example, they can be selectively and covalently bound to solid surfaces or to other relevant molecules, or so that they can be bound by other interactions such as, e.g. hydrogen bonding, van der Waals forces, etc. Sometimes, molecules that permit selective purification of the conjugate are used but are separated from the actual oligonucleotide later on. "Methods of Molecular Biology 26: Protocols for Oligonucleotide Conjugates (Sudir Agrawal, ed.) Humana Press, Totowa, N.J., 1994 (ISBN: 0-89603-252-3)" provides a very good review of common methods for producing oligonucleotide conjugates.

Phosphite amide derivatives of the desired haptenes are often used as reagents to save time because they are easy to employ in common automatic devices for DNA synthesis and they do not require a specially qualified operator. Their reaction products must be purified in the usual manner. However, each haptene requires a specific reagent, which, in comparison to the basic haptene itself, is unreasonably expensive, often relatively unstable, and many times does not produce the high reaction yields that are expected when compared with DNA phosphite amide agents. Excess reagent and product residues, that always result when only a small fraction of the desired specifically labeled oligonucleotides is produced, must be removed and discarded within a short time period and contribute further to the poor efficiency of these reagents. As a result, the costs of modified oligonucleotides are usually dominated by the costs of the functionalizing reagents.

Therefore, it is an object of the present invention to provide an inexpensive and universally applicable method for introducing labels into oligonucleotides that avoids the disadvantages of the methods of the prior art. Also, the method of the present invention requires little expertise and allows for linking any oligonucleotide building block to a large number of commercially available and inexpensive haptenes with a minimum of or no waste products.

This object is solved by a method for the manufacture of labeled oligonucleotide conjugates comprising the reaction of (a) an oligonucleotide on a solid support having a labile orthogonal protecting group bound to a terminal hydroxy group, and (b) a labeling compound, wherein said labile protecting group is partially or completely substituted by said labeling compound in a nucleophilic substitution reaction.

Said method permits simple access to thermodynamically and kinetically stable labeled oligonucleotide conjugates.

Oligonucleotides are characterized in that they have at least two nucleoside building blocks linked via a phosphoric ester. Optionally, the phosphoric ester may be protected or unprotected. The phosphoric ester may be a phosphoric diester, a phosphoric triester or even an H-phosphonate. When bound to a solid phase, the oligonucleotide can either be structured in a 3'-5' direction or a 5'-3' direction relative to the solid phase. The bases of the nucleosides within the oligonucleotide may be protected or unprotected, although protected bases are preferred. It is to be noted that any oligonucleotide compounds may be used for conjugate synthesis according to the invention as long as they can be modified to carry a labile protecting group on a terminal hydroxy group, preferably on a 3'- or 5'-terminal hydroxy group. RNA, PNA, LNA, alkane phosphonate DNA and derivatives and mixtures thereof are examples of oligonucleotides suitable for practicing the present invention. RNA or DNA is preferred, DNA is more preferred. Oligonucleotide synthesis is common in the art so that the provision of any desired oligonucleotides is routine work and will not be elaborated further herein.

The method of the present invention preferably uses oligonucleotides and polynucleotides that comprise or consist of at least 2 to 100 nucleosides, particularly 8 up to 70 nucleosides, preferably up to 30 nucleosides, more preferably up to 25 nucleosides and most preferably up to 20 nucleosides. Also preferred is that oligonucleotides for use in the invention consist of 8 to 70, most preferably 8 to 30 nucleosides.

The term "conjugate" as used herein refers to molecules comprising at least two different building blocks, one of them being an oligonucleotide as defined above, the other being a labeling compound that has physical, chemical, and/or biological properties that differ from those of the oligonucleotide.

The term "labeling compound" is defined as any compound that is suitable to identify said oligonucleotide being part of said conjugate by those features in the oligonucleotide conjugate that go beyond the features of the oligonucleotide itself. Labeling compounds according to the present invention can have very different structural features. For example, the label may be more or less hydrophobic than the oligonucleotide, or it can be optically active; it may add to the molecular weight of the oligonucleotide in a characteristic way, so that the determination of the conjugates weight serves to identify the oligonucleotide, e.g. by mass spectroscopy; it may provide antigenically reactive properties to allow identification by specific antibodies; it may allow for radioactive emission; it may allow for binding of the conjugate to hydrophobic, hydrophilic or otherwise reactive identification reagents; etc. Because of the above, it is obvious, that labeling compounds suitable for the method of the present invention cannot be described by simply listing particular technical features but must be defined by their function. The labeling agent must be capable of providing a distinguishing, i.e. labeling, feature to the conjugate and it must further be capable of nucleophilically substituting a labile protecting group on a terminal hydroxyl group of the oligonucleotide to result in the desired conjugate.

Preferably, the label in the conjugate can be detected by fluorescence, phosphorescence, luminescence, elevated and specific UV/VIS, IR absorption, mass spectrometry-specific detectability, or affinity detection by secondary mechanisms such as antibodies, colored or fluorescent nanoparticles, molecular bar codes and the like. Fluorescence extinguishers such as dinitrophenols are also preferred as labels.

In a preferred embodiment, the labeling compound is selected from the group consisting of enzymes, optically active compounds, antigenic epitopes, radioactive compounds, metal chelates, dyes, linker moieties, spacer moieties, charged residues, isotopically enriched mass labels, peptides, proteins, silicones, biotin, hydracids, lipids, steroids, multinuclear aromatic or, as applicable, heteroaromatic systems such as naphthalenes, anthracenes, xanthones, thioxanthones, acridones and the correspondingly substituted derivatives thereof as well as dinitrophenols, azobenzenes, psoralenes, fluoresceins, acridines, thiazoles, cyanines, coumarins and the correspondingly substituted derivatives thereof. Other preferred labeling compounds that can be used are monofunctional, bifunctional or polyfunctional long-chain or branched-chain alkanes, dendrimers, alkoxyalkyl compounds and, in particular, polyethylene glycols.

In a further preferred embodiment, the labeling compound comprises a reactive group selected from the group consisting of SH, OH, and NRH for nucleophilically substituting the labile protection group of the oligonucleotide.

In a more preferred embodiment, said NRH-group is part of a homocyclic, heterocyclic, homoaromatic, or heteroaromatic system, R being H, alkyl, substituted or unsubstituted cycloalkyl, substituted or unsubstituted aryl, substituted or unsubstituted alkylaryl.

An orthogonal labile protecting group for practicing the present invention is any protecting group that can be introduced to protect a hydroxyl moiety of an oligonucleotide, preferably a terminal hydroxyl group, more preferably a 3'- and/or 5'-hydroxyl group, and that can also be cleaved without altering the compound in an undesired way. Protection, as is well known, means masking said hydroxy group from undesired reagents. Of course, the protecting group depends on the nature of the undesired reagent and the reaction conditions. A protection group must be capable of being introduced without interfering with other moieties and it must be capable of being cleaved without altering the protected substance. Many structurally different reagents are known for protecting oligonucleotides. Those, that are useful for practicing the present invention, must be capable of being substituted by nucleophilic reagents, preferably labelling reagents that comprise SH-, OH- and/or NRH-reactive groups.

In a further preferred embodiment, said labile orthogonal protecting group is selected from carbonate esters or thionocarbonate esters or N-alkylimidylcarbonate esters or dithiocarbonate esters or thiocarbamates of nitrophenyl, subst. nitrophenyl, pentahalogenphenyl, tetrahalogenphenyl, pyridyl, subst. pyridyl, N-alkyl-pyridinium-yl, imidazolyl, subst. imidazolyl, N-alkylimidazolyl, triazolyl, subst. triazolyl, tetrazolyl.

In a preferred embodiment, said oligonucleotide is bound to a solid phase at the 3'-end and the terminal hydroxyl group is the 5'-hydroxy group.

In a further preferred embodiment, said oligonucleotide is bound to a solid phase at the 5'-end and the terminal hydroxyl group is the 3'-hydroxy group.

In a preferred embodiment of the method of the present invention, the oligonucleotide conjugate is partially deprotected by the reaction. The term "partially deprotected" means that a part of the labile protecting group remains in the conjugate after nucleophilic substitution by the labeling compound.

The oligonucleotide conjugate obtained by the method of the present invention can be used for molecular-biological and biochemical assays. The conjugates are stable and readily available with a high degree of purity and as such easy to store without any particular precautions.

Surprisingly, the labeled nucleoside phosphite amide synthones provided by the invention are at least as stable as conventional phosphite amides that result from DNA synthesis in automatic devices. The stability of the conjugates applies to both the dry substance and a solution thereof. Furthermore, high coupling yields can be obtained without any modification of the conditions for the synthesis of normal phosphite amides. Moreover, preparation of synthones is fairly simple and inexpensive, so that the costs of these reagents are only insignificantly higher than those observed for normal synthesis, about a factor 2, e.g., the cost of biotin phosphite amide is a factor 5 higher when compared to biotin hydrazide; the cost of fluorescein phosphite amide is a factor 35 higher when compared to fluorescein amine, and the cost of hexaethylene glycol phosphite amide is even higher by a factor of 100 when compared to hexaethylene glycol.

The high reaction rate of the nucleophilic substitution is also surprising, because it makes reactions possible that are almost quantitative in yield, said reactions taking place, e.g., within 1-2 minutes, when a nitrophenyl carbonate is used together with amines at room temperature, and within 5-10 minutes, if primary alcohols are subjected to DMAP catalysis. These reaction times and yields are especially advantageous for the user because they permit a high throughput with low technical requirements, e.g. simple purification by filtration in an automatic device for DNA synthesis can be used. Moreover, the nitrophenylate leaving group in the NPC derivative can be conveniently determined for spectrophotometric estimation of the reaction yield.

In summary, it is convenient, inexpensive and very easy to manufacture oligonucleotide conjugates according to the present invention, in particular when using N-methyl aminopropyl trimethoxy silane and pyrene methanol as shown in the implementation examples below.

Preferred embodiments of the present invention are further described in the drawings wherein:

FIG. 1 shows an exemplary non-limiting synthesis scheme for the manufacture of oligonucleotide conjugates.

This FIGURE shows an exemplary and non-limiting diagram of a synthetic strategy for the manufacture of oligonucleotide conjugates (3) according to the method of the present invention.

In this process, a solid-phase bound oligonucleotide (1) having protecting groups P as defined below is reacted with an $NH_2$-nucleophilic label compound (2). The solid phase S may be any solid substrate that is commonly used in oligonucleotide chemistry. The substrate in FIG. 1 is represented by the letter S, with the oligonucleotide (1) being bonded either covalently to substrate S or being bonded or attached by other mechanisms commonly used in oligonucleotide chemistry. Typical linkers and spacer groups may also be arranged between the oligonucleotide and the substrate S.

The particular oligonucleotide (1) comprises at least two nucleosides linked via a phosphoric ester (n=1), one of which, for example, is a nucleoside according to the formula (X), in which the terminal nucleoside has the meaning shown in compound (1) and which can be linked both via 3'-5' phosphoric acid ester linkages and 5'-3' phosphoric acid ester linkages:

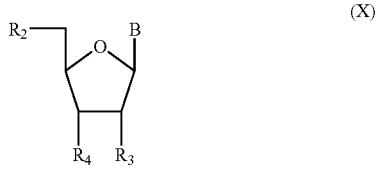

(X)

wherein the letter B stands for adeninyl, cytosinyl, guaninyl, thyminyl, uracilyl, 2,6-diaminopurine-9-yl, hypoxanthine-9-yl, 5-methocytosine-1-yl, 5-amino-4-carboxylimidazole-1-yl or 5-amino-4-carbamoylimidazole-1-yl in compound (X) and the terminal nucleoside, with the primary amino functions of B having a permanent protecting group P commonly used in oligonucleotide chemistry or, as applicable, thyminyl or uracilyl having a permanent protecting group P commonly used in oligonucleotide chemistry in the $O_4$ position, $R_2$ may be a phosphoric acid ester residue, a free hydroxy group, a phosphite amidoester, a phosphonic acid ester residue or another suitable hydroxy protecting group, $R_3$ may be H, OH, halogen, an acylamino, alkoxy or alkoxy alkyl residue with 1 to 4 carbon atoms, $R_4$ may be a phosphoric acid ester residue, a free hydroxy group, a phosphite amidoester residue, a phosphoric acid ester residue, an H phosphonate residue or a hydroxy protecting group, and wherein the motive L-Y in formula (I) is a leaving group commonly used in oligonucleotide chemistry, with Y=O, methyl, ethyl or propyl, X=O, S, Se or Te and n may be an integer from 1 to 10, with n=1 to 4 being preferred.

The term "nucleotide" in Compound (1) means a nucleoside as defined above that contains at its 5' position a phosphoric residue according to the definition of $R_2$. The letter P also has the meaning as defined above.

Compound (1) is easily accessible by methods used in oligonucleotide synthesis chemistry which are known to those skilled in the art. Of course, other oligonucleotides may also be used within the scope of the invention.

Compound (2) substitutes the L-Y leaving group in Step I in a nucleophilic manner, thus forming compound (3), with excess $NH_2$ label and L-Y being removed readily by filtration. In Step II, Compound (3) is deprotected subsequently by common means known to those skilled in the art, thus forming a deprotected oligonucleotide conjugate (4) that can be stored and is extremely stable. Depending on the protecting groups and the reaction conditions used, partial deprotection, i.e. of base B or the nucleotide residue alone, is also possible.

Below, the invention will be explained by means of examples. These examples only serve to explain the invention and do not limit the general spirit of the invention in any way.

EXAMPLES

Abbreviations

DMT dimethoxytrityl
NPC 4-nitrophenyloxycarbonyl
TAC tert. butylphenoxyacetyl
RT retention time
TEAAC triethylammoniumacetate
ACN acetonitrile
DMAP 4-dimethylaminopyridine Example 1

Two oligonucleotides having the following sequences were synthesized in an automatic device for DNA synthesis (Applied Biosystems, Model 392):

```
Oligonucleotide 1:
5'-d(TGC TCG CTG T)-3'

Oligonucleotide 2:
5'-d([NPC-T]GC TCG CTG T)-3'
```

In the case of C and G, standard β-cyanoethyl diisopropylamino phosphoramidites from Perseptive Biosystems with TAC as base protecting group and DMT as a 5' protecting group were used as synthones in the synthesis. In the case of oligonucleotide 2, the last T introduced was β-cyanoethyl diisopropylamino phosphoramidite of T with a 5'-p-nitrophenyl carbonate function [NPC thymidine amidite].

When DMT protected synthones were used, an average coupling yield per synthesis step of more than 98% was detected by the automatic synthesizing device.

A synthesis scale of 0.4 (micromolar) was used and a standard synthesizing program recommended by the manufacturer was carried out.

Results:

Oligomer 1:

For synthesizing oligomer 1, synthesis was conducted by manual deprotection using ammonia in a trityl-off manner, resulting in the desired oligonucleotide with a purity of 98% (determined via HPLC (RT=8.17 min)).

Oligomer 2:

For synthesizing oligomer 2, synthesis was conducted in a trityl-off manner and the solid substrate was removed from the synthesis column, divided into three portions almost similar in size (2a, 2b, 2c) and transferred to Eppendorf reaction tubes.

The individual portions, 2a, 2b and 2c, were then treated as follows:

2a: 15-minute reaction with an anthracene stock solution (10 µl) in 90 µl acetonitrile with occasional shaking. Then, 200 µl of concentrated ammonia were added, and the solution was left standing at room temperature all night to remove the base protecting groups and separate the oligonucleotide conjugate from the substrate.

2b: 30-minute reaction with an anthracene stock solution (50 µl) in 50 µl acetonitrile with occasional shaking. Then, 200 µl of concentrated ammonia were added, and the solution was left standing at room temperature all night to remove the base protecting groups and separate the oligonucleotide conjugate from the substrate.

2c: Addition of 200 µl concentrated ammonia; the solution was left standing at room temperature all night to remove the base protecting groups, separate the oligonucleotide conjugate from the substrate and convert the underivatized NPC- back into the free OH function.

The anthracene stock solution (in acetonitrile) consisted of 0.5 mol N-methyl(aminomethyl) anthracene and 0.2 mol dimethyl aminopyridine.

In all three examples, 2a, 2b and 2c, the supernatant solution was then decanted from the substrate, rinsed with water, and the joined solutions were concentrated to dryness in a Savant SC 210 speed vac system. After renewed dissolution of the residue in a buffer solution, Examples 2a, 2b and 2c were analyzed by means of HPLC with the following results: (RT values are in minutes, column type: RP-18 Merck Lichrosphere 125×4, pump type: L-7100 (Merck-Hitachi), solvent A: TEAAC, solvent B, C: ACN).

Example 2a

A DMAP peak appeared at 2.37 minutes, a nitrophenol peak at 13 minutes and an anthracene peak at 29 minutes, whereas both the by-products of the reaction and the unreacted oligonucleotide sequences appeared at approx. 8 minutes. The oligonucleotide conjugate peak appeared at 15.8 minutes with the anthracene unit coupled to its 5'-end as carbamate and easy to determine due to the intensive fluorescence of this peak. Reaction was approx. 90%.

Example 2b

The DMAP peak appeared at 2.13 minutes, the nitrophenol peak at 13 minutes and the anthracene peak at 29 minutes, whereas both the by-products of the reaction and unreacted oligonucleotide sequences appeared at approx. 7 minutes. The oligonucleotide conjugate peak appeared at 15.8 minutes, with the anthracene unit coupled to its 5'-end as carbamate and able to be determined due to the fluorescence of this peak. Reaction was more than 95%.

Example 2c

The nitrophenol peak appeared at 13 minutes, the by-products of the reaction and the unreacted oligonucleotide sequences at approx. 7 minutes. The oligonucleotide appeared at 8.17 minutes and exhibited the same sequence as Oligonucleotide 1. Identification was achieved by simultaneous injection of both products (oligonucleotide and Example 2c), which resulted in the same peak. Reaction was more than 98%.

This reaction demonstrates that an underivatized NPC oligonucleotide, i.e. an NPC group not reacted with a haptene, reacts fully to again form underivatized initial OH oligonucleotides during ammonia protecting group separation/total deprotection, to the effect that it does not interfere with subsequent reaction or purging steps.

Example 2

The 5'-p-nitrophenyl carbonate of thymidine [NPC thymidine] was reacted with the following compounds:

1. 2-(2-nitrophenyl) propane-1-ol under DMAP catalysis in dichloromethane

2. Pyrenyle methanol under DMAP catalysis in dichloromethane 3. 4-chlorophenyl hydrazine with DMAP 1.1 equivalents in dichloromethane 4. Acetyl hydrazine in dichloromethane 5. N-methyl aminopropyl trimethoxy silane in DMF 6. Fluorene methanol with DMAP catalysis in toluene 7. Allyl alcohol with DMAP catalysis in dichloromethane 8. 2,2,2-trichloroethanol with DMAP catalysis in dichloromethane Reaction time was 5-60 minutes at room temperature, with approx. 1.2 equivalents of reaction partners based on NPC-T being used.

The reaction products were analyzed by means of thin-layer chromatography and each time, the analysis showed a quantitative reaction in which carbamate or carbonate was formed. The reaction was easy to follow due to the increasing yellow coloring caused by the nitrophenolate anion released.

The products of Reactions 1, 6, 7, and 8 yielded reaction products that were identical to comparative examples obtained by direct reaction with the corresponding chloroformiates.

The products of Reactions 2, 3 and 4 were characterized by their NMR spectra. It must be noted that the product of Reaction 2 cannot be obtained using the corresponding chloroformiate.

It was not possible to purify and isolate the product of Reaction 5 due to its hydrolytic decomposition and simultaneous formation of insoluble oligomeric silicones. When samples from the reaction mixture in Reaction 5 were placed on a silica thin-layer chromatography plate and heated for one minute before trying to develop the chromatography, the compound was already immobilized on the silica, so that no migration of the reaction products took place, even when a very polar mobile phase was used.

Thus, the reaction product of Reaction 5 is particularly well suited for anchoring oligonucleotide sequences on solid substrates.

The invention claimed is:

1. A method for the manufacture of an oligonucleotide conjugate comprising reacting,
   (a) an oligonucleotide on a solid support comprising a labile orthogonal protecting group that is bound to a terminal hydroxy group, and
   (b) a labeling compound,
wherein said labile orthogonal protecting group is at least partially substituted by said labeling compound in a nucleophilic substitution reaction.

2. The method according to claim 1, wherein the labeling compound is a peptide, an enzyme, an optically active compound, a metal chelate, a dye, a linker moiety, a spacer moiety, a charged reside, an isotopically-enriched mass label, a protein, a silicone, biotin, a hydracid, a lipid, a steroid, a multinuclear aromatic or heteroaromatic system, a long-chain or branched-chain alkane, a dendrimer, or an alkoxy alkyl compound.

3. The method according to claim 2, wherein the labeling compound contains a reactive group which is SH, OH or NRH.

4. The method according to claim 3, wherein said NRH- group is part of a homocyclic, heterocyclic, homoaromatic, or heteroaromatic system, wherein R is H, alkyl, substituted or unsubstituted cycloalkyl, substituted or unsubstituted aryl, substituted or unsubstituted alkylaryl.

5. The method according to claim 1, wherein said labile protecting group is a carbonate ester, a thionocarbonate ester, an N-alkylimidylcarbonate ester, a dithiocarbonate ester, a thiocarbamate of nitrophenyl, a substituted nitrophenyl, pentahalogenphenyl, a tetrahalogenphenyl, a pyridyl, a substituted pyridyl, an N alkyl-pyridinium-yl, an imidazolyl, an N-alkylimidazolyl, a triazolyl, a substituted triazolyl, or a tetrazolyl group.

6. The method according to claim 1, wherein the oligonucleotide and the resulting conjugate is bound to a solid phase at the 3'-end and the terminal hydroxyl group is the 5'-hydroxy group.

7. The method according to claim 1, wherein the oligonucleotide and the resulting conjugate is bound to a solid phase at the 5'-end and the terminal hydroxyl group is the 3'-hydroxy group.

8. The method according to claim 1, wherein the oligonucleotide conjugate is only partially deprotected by said nucleophilic reaction.

9. The method according to claim 1, wherein the labeling compound is a naphthalene, an anthracene, a xanthone, a thioxanthone, an acridone, a dinitrophenol, an azobenzene, a psoralene, a fluorescein, an acridine, a thiazole, a cyanine, a coumarin or a substituted derivative thereof or a polyethylene glycol.

* * * * *